United States Patent [19]

Vattuone

[11] Patent Number: 5,655,541
[45] Date of Patent: Aug. 12, 1997

[54] FINE NEEDLE CYTOLOGY ASPIRATION DEVICE

[76] Inventor: John R. Vattuone, 211 Fox Meadow Rd., Scarsdale, N.Y. 10583

[21] Appl. No.: 365,922

[22] Filed: Dec. 29, 1994

[51] Int. Cl.⁶ ..................................................... A61B 10/00
[52] U.S. Cl. ................................................. 128/749; 604/197
[58] Field of Search ................................. 128/752, 753, 128/748, 760, 749; 604/205, 207, 246, 197, 198

[56] References Cited

U.S. PATENT DOCUMENTS

| | | | |
|---|---|---|---|
| 3,774,604 | 11/1973 | Danielsson | 604/169 |
| 3,834,372 | 9/1974 | Turney | 128/748 |
| 4,543,094 | 9/1985 | Barnwell | 604/236 |
| 4,549,554 | 10/1985 | Markham | 128/753 |
| 4,619,272 | 10/1986 | Zambelli | 128/753 |
| 4,857,061 | 8/1989 | Miller | 604/207 |
| 4,967,762 | 11/1990 | DeVries | 128/753 |
| 4,972,843 | 11/1990 | Brodén | 128/760 |
| 5,097,842 | 3/1992 | Bonn | 128/762 |
| 5,104,381 | 4/1992 | Gresl et al. | 604/164 |
| 5,127,904 | 7/1992 | Loo et al. | 604/83 |

*Primary Examiner*—Max Hindenburg
*Assistant Examiner*—Pamela L. Wingood
*Attorney, Agent, or Firm*—Richard C. Litman

[57] ABSTRACT

The present invention is a fine needle cytology aspiration device having a sliding valve which allows the vacuum in the needle to be released and also the sample to be withdrawn without contamination while allowing the surgeon to use only one hand for carrying out these operations. Further, a protective sheath is described which reduces the risk of needle-stick injuries.

3 Claims, 2 Drawing Sheets

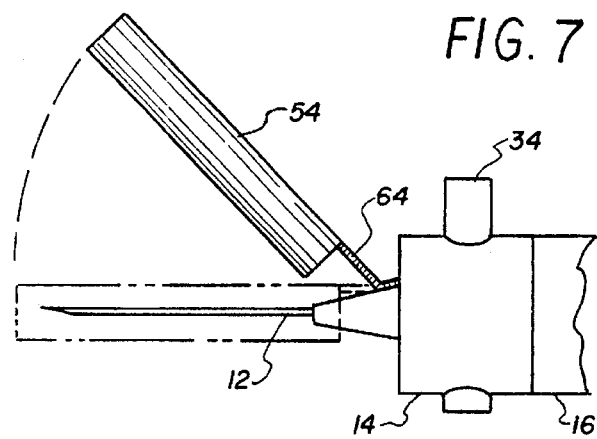
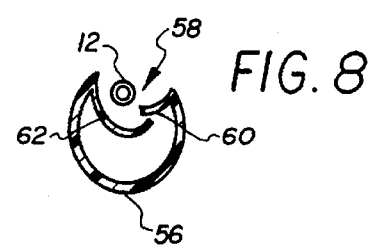
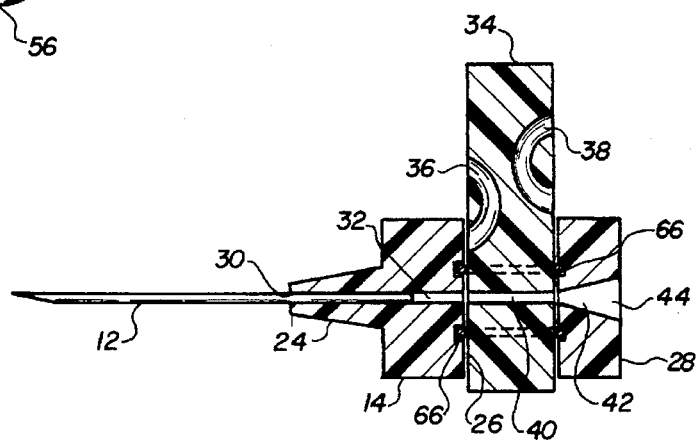
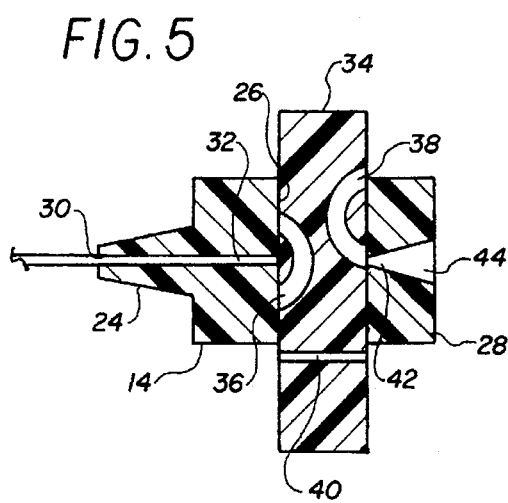
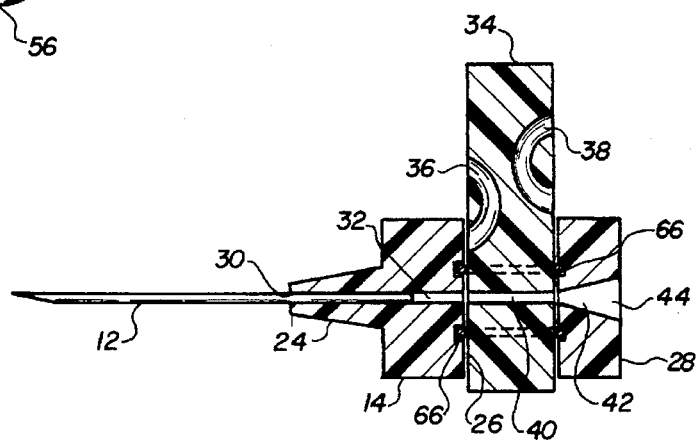

FINE NEEDLE CYTOLOGY ASPIRATION DEVICE

BACKGROUND OF THE INVENTION

1. Field of the Invention

The present invention relates to a fine needle cytology aspiration device for removing tissue and body fluid samples from a patient.

2. Description of the Prior Art

In fine needle cytology aspiration it is necessary to draw body fluid and tissue samples for later analysis without allowing the samples to be contaminated with fluids or tissues from non-target locations as the needle is withdrawn. For this reason, fine needle cytology aspiration devices which allow the breaking of the vacuum in the device before the needle is withdrawn have been proposed in the prior art.

U.S. Pat. No. 4,967,762, issued to DeVries, shows a fine needle aspiration device which uses a rubber O-ring to seal vents which can be used to release the vacuum in the needle.

U.S. Pat. No. 4,543,094, issued to Barnwell, U.S. Pat. No. 5,104,381, issued to Gresl et al., U.S. Pat. No. 3,834,372, issued to Turney, U.S. Pat. No. 4,619,272, issued to Zambelli, and U.S. Pat. No. 3,774,604, issued to Danielsson, all show rotating valves for medical applications. All the devices shown in the above cited patents suffer from the drawback that they require two hands for their operation.

U.S. Pat. No. 5,127,904, issued to Loo et al., shows an infusion system having an injection port for administering medications.

U.S. Pat. No. 4,857,061, issued to Miller, shows a syringe having a one-way valve which a swinging flap. Miller does not show the sliding valve of the present invention.

U.S. Pat. No. 5,097,842, issued to Bonn, shows a sliding valve which only has two internal channels and does not provide for venting the system to the atmosphere.

None of the above inventions and patents, taken either singly or in combination, is seen to describe the instant invention as claimed.

SUMMARY OF THE INVENTION

The present invention is a fine needle cytology device that uses a sliding valve to selectively draw a tissue or fluid sample, and separately vent the needle and the syringe barrel, while requiring the use of only one hand for its operation.

Accordingly, it is a principal object of the invention to provide a fine needle cytology aspiration device which can be operated with one hand.

It is another object of the invention to provide a fine needle cytology aspiration device which allows for independent venting of the needle and the syringe to the atmosphere.

It is a further object of the invention to provide a fine needle cytology aspiration device which does not allow contamination of the sample as the needle is withdrawn from a patient's body.

Still another object of the invention is to provide a fine needle aspiration device having a protective sheath to reduce the risk of needle-stick injury and consequent disease transmission.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIGS. 2–5 show the fine needle cytology aspiration device of the present invention in cross section, with the sliding member of the valve portion in various positions.

FIG. 7 is an elevational view showing the protective sheath moved to the side to allow device use.

FIG. 8 is a cross section of the protective sheath with the needle aligned with the slit.

FIG. 9 is a cross section of the protective sheath showing the needle housed therein.

FIG. 10 is a cross section of the valve portion showing the sealing O-rings.

Similar reference characters denote corresponding features consistently throughout the attached drawings.

DETAILED DESCRIPTION OF THE PREFERRED EMBODIMENT

Figure 1:
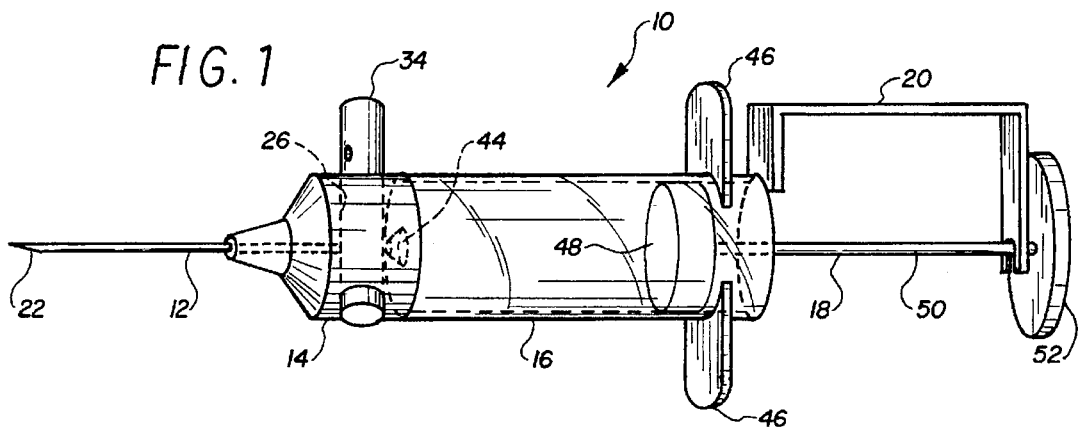
FIG. 1 is a perspective view of the fine needle cytology aspiration device of the present invention.
Figure 2:
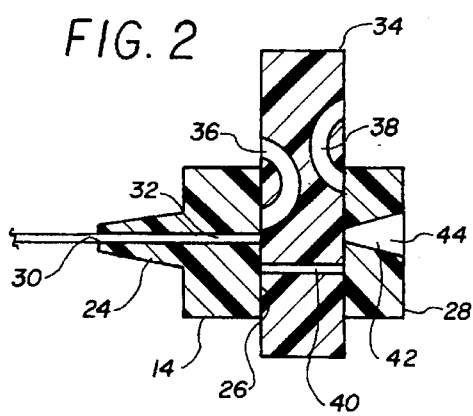

Referring to FIG. 1, the present invention is a fine needle cytology aspiration device 10 which includes a penetrator portion or needle 12, a valve portion 14, and a syringe portion. The syringe portion includes a barrel 16, plunger 18, and plunger holder 20.

The needle 12 is in the form of a hollow cylindrical tube having a lumen, and a penetrating end 22 formed by cutting the tube at an angle to form a sharp cutting point adjacent an ellipsoidal opening.

Referring to FIGS. 2–5, the valve portion 14 has a first end 24, a transverse channel or fore 26, and a second end 28. The first end 24 of the valve portion 14 has an opening 30 to allow communication with the lumen of needle 12. One end of the needle 12 is secured to the first end 24 of the valve portion 14. A channel 32 extends from the opening 30 to the transverse fore 26.

Slidably positioned within transverse fore 26 is a sliding member 34. A portion of the sliding member 34 protrudes from valve portion 14 at all times to allow the sliding member 34 to be moved along transverse fore 26 by finger pressure. Sliding member 34 has three internal channels 36, 38, and 40. Each of these three internal channels extends between a corresponding first opening and a corresponding second opening. Internal channel 40 is a straight channel passing diametrically through sliding member 34. Channel 36 is an arcuately configured channel having openings laterally spaced along the surface of the sliding member, and channel 38 is an arcuate channel with openings laterally spaced along the opposite surface of said sliding member 34.

The second end 28 of the valve portion 14, has a second channel 42 extending between the transverse channel 26 and an opening 44. The second end 28 of the valve portion 14 is attached to the syringe barrel 16, and the opening 44 is in communication with the interior of the barrel 16 as shown in FIG. 1.

The syringe barrel 16 is normally provided with finger extensions 46 which facilitate the grasping of the device 10 when moving the plunger 18.

The plunger 18 has a piston portion 48, a shaft 50, and a gripping portion 52. The piston portion 48 is preferably made of rubber, and is sized to snugly fit into the bore of the barrel 16 so as to seal the volume defined by the piston portion 48 and the bore of the barrel 16 from the ambient atmosphere. The gripping portion 52 facilitates the grasping of the plunger 18 by a user when slidably moving the plunger 18 within the barrel 16.

The plunger holder or bracket 20 is positioned between the end, distal from needle 12, of the barrel 16 and the gripping portion 52 of the plunger 18 when it is desired to prevent movement of the plunger 18 into the barrel 16 due to the suction force generated by the vacuum in the barrel bore.

In operation, the plunger 18 is first moved fully forward. Then the sliding member 34 is put into the position shown in FIG. 2. In this position, the sliding member 34 completely seals off the space defined by the bore of barrel 16 and the piston portion 48. The plunger 18 is then withdrawn to the desired position creating a vacuum within the bore of barrel 16. Atmospheric pressure tends to force the plunger 18 back into the bore of barrel 16. Therefore, the bracket 20 is interposed between the barrel 16 and the gripping portion 52 to hold the plunger 18 in place.

The needle 12 is then inserted into the desired position within the patient's body. Sliding member 34 is then moved to the position shown in FIG. 4. With sliding member 34 in this position, channel 40 has one end in registry with channel 32 and the other end in registry with channel 42, thus allowing the vacuum in barrel 16 to draw body fluid and tissue samples into the bore of barrel 16.

Figure 3:
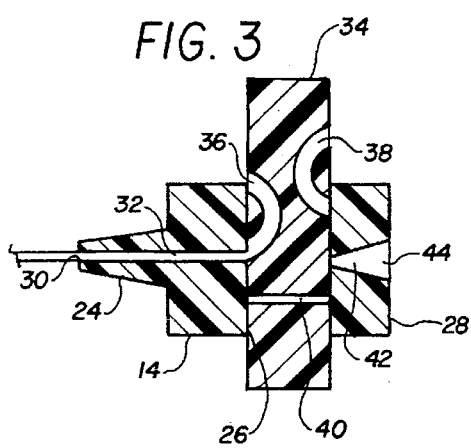
Figure 4:
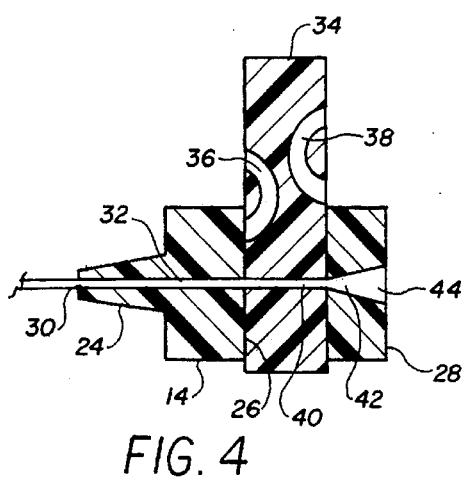

Once the desired amount of fluid or tissue has been withdrawn, the sliding member 34 is moved to the position shown in FIG. 3. With sliding member 34 in this position, channel 36 has one end in registry with channel 32 and the other end open to the atmosphere, thus releasing the suction on the lumen of needle 12 and allowing easy retrieval of needle 12.

To expel the sample from barrel 16, the sliding member 34 is first moved to the position shown in FIG. 5. In this position, one end of channel 38 is in registry with channel 42 and the other end is open to the atmosphere, thus releasing the vacuum in the bore of barrel 16. The plunger holder 20 is then removed and the sliding member 34 moved back to the position shown in FIG. 4. Now moving the plunger forward within the bore of barrel 16 expels the sample from the barrel 16 for analysis.

Figure 6:
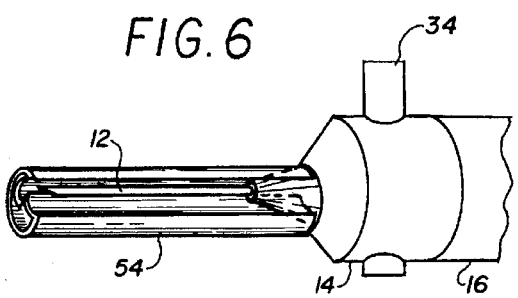
FIG. 6 is a partial perspective view showing the protective sheath of the present invention with the needle aligned with the side slit.

To enhance the safety of the device 10, the protective sheath 54 shown in FIG. 6 can be provided at the first end 24 of the valve portion 14. The protective sheath 54 is made of a plastic tube 56 having a longitudinal slit 58 along the side thereof as best shown in FIGS. 8 and 9. Resilient flaps 60 and 62 act as closures for the tube 56. When not in use the needle 12 is pressed against the flaps 60 and 62 until the flaps part sufficiently to allow the needle 12 to enter the lumen of tube 56. The flaps 60 and 62 then spring back to their original positions thus enclosing needle 12 within protective sheath 54. The protective sheath 54 is attached to first end 24 of valve portion 14 by a resilient strip 64 as shown in FIG. 7.

Preferably, a pair of O-rings 66 shown in FIG. 10 are provided within the transverse channel 26 in order to seal any gap between sliding member 34 and transverse channel 26.

Although the preferred embodiment is shown as being of unitary construction the valve member 14 can be made to have standard type attachments for receiving standard needles and syringes at its respective ends.

It is to be understood that the present invention is not limited to the sole embodiment described above, but encompasses any and all embodiments within the scope of the following claims.

I claim:

1. A fine needle cytology aspiration device comprising:

a hollow needle having an ellipsoidal opening at one end;

an elongated barrel having an open end with an interior cavity containing a plunger and an opposite end including a valve portion;

said valve portion having a first channel in communication with said hollow needle, a second channel longitudinally aligned with said first channel and in communication with the interior cavity of said barrel, and a transverse bore passing latitudinally through the valve portion; and a cylindrical sliding member slidably movable and positioned within said transverse bore, said sliding member having end portions protruding from said traverse bore and three separate internal channels, said internal channels consisting of a straight channel passing diametrically through said sliding member whereby the said straight channel can create a passage from said hollow needle to said internal cavity of said barrel, a first arcuate channel having first openings laterally spaced along a first surface of said sliding member, whereby said first arcuate channel can release the suction within said needle when it is opened to the atmosphere and a second arcuate channel having second openings laterally spaced along a second opposite surface of said sliding member whereby said second arcuate channel can release the vacuum in the bore of said barrel when the other end is open to the atmosphere.

2. The cytology aspiration device according to claim 1, wherein said plunger includes a shaft having a piston element at one end thereof snugly mounted within the interior cavity of said barrel and a grip member extending through said open end of the barrel.

3. The cytology aspiration device according to claim 2, further including a bracket positioned between said open end of the barrel and said grip member, whereby the bracket holds said plunger in place when a vacuum is created within the interior cavity of the barrel.

* * * * *